(12) United States Patent
Ibáñez Català

(10) Patent No.: US 10,537,263 B2
(45) Date of Patent: Jan. 21, 2020

(54) ATRIAL FIBRILLATION DETECTION SYSTEM AND METHODS OF USE

(71) Applicant: Smart Solutions Technologies, S.L., Madrid (ES)

(72) Inventor: Xavier Ibáñez Català, Valencia (ES)

(73) Assignee: Smart Solutions Technologies, S.L., Madrid (ES)

( * ) Notice: Subject to any disclaimer, the term of this patent is extended or adjusted under 35 U.S.C. 154(b) by 368 days.

(21) Appl. No.: 15/369,880

(22) Filed: Dec. 5, 2016

(65) Prior Publication Data

US 2017/0156614 A1 Jun. 8, 2017

(30) Foreign Application Priority Data

Dec. 7, 2015 (ES) .................................. 201531775

(51) Int. Cl.
*A61B 5/04* (2006.01)
*A61B 5/046* (2006.01)
*A61B 5/00* (2006.01)
*A61B 5/024* (2006.01)
*A61B 5/0245* (2006.01)
*A61B 5/044* (2006.01)
*A61B 5/0452* (2006.01)

(52) U.S. Cl.
CPC ............ *A61B 5/046* (2013.01); *A61B 5/0006* (2013.01); *A61B 5/0245* (2013.01); *A61B 5/02405* (2013.01); *A61B 5/044* (2013.01); *A61B 5/04012* (2013.01); *A61B 5/04525* (2013.01)

(58) Field of Classification Search
CPC ... A61B 5/046; A61B 5/04525; A61B 5/0006; A61B 5/04012; A61B 5/0245; A61B 5/02405; A61B 5/044; A61B 5/7262
See application file for complete search history.

(56) References Cited

U.S. PATENT DOCUMENTS 6,377,844 B1  4/2002  Graen
2008/0161703 A1  7/2008  Houben et al.

OTHER PUBLICATIONS

Sarkar, et al., "Communications—A Detector for a Chronic Implantable Atrial Tachyarrhythmia Monitor," IEEE Transactions on Biomedical Engineering, (2003), vol. 55, No. 3.
Zhang, et al., "Automatic recognition of cardiac arrhythmias based on the geometric patterns of Poincare plots," Physiol. Meas., No. 36 (2015), pp. 283-301.

*Primary Examiner* — Mallika D Fairchild
(74) *Attorney, Agent, or Firm* — Entralta P.C.; Justin G. Sanders; Peter D. Weinstein

(57) ABSTRACT

An atrial fibrillation detection system and associated methods of use are disclosed for analyzing and identifying atrial fibrillation signs of a user. In at least one embodiment, the system includes an at least one computing device configured for receiving and processing an at least one biosignal associated with heart activity of the user as captured by an at least one beat detector, and subsequently transmitting said processed at least one biosignal, as a plurality of sequence segments, making up an at least one interbeat interval sequence of the biosignal, to an at least one classifier configured for determining a probability of the at least one interbeat interval sequence of the biosignal being an atrial fibrillation rhythm or a non-atrial fibrillation rhythm.

20 Claims, 6 Drawing Sheets

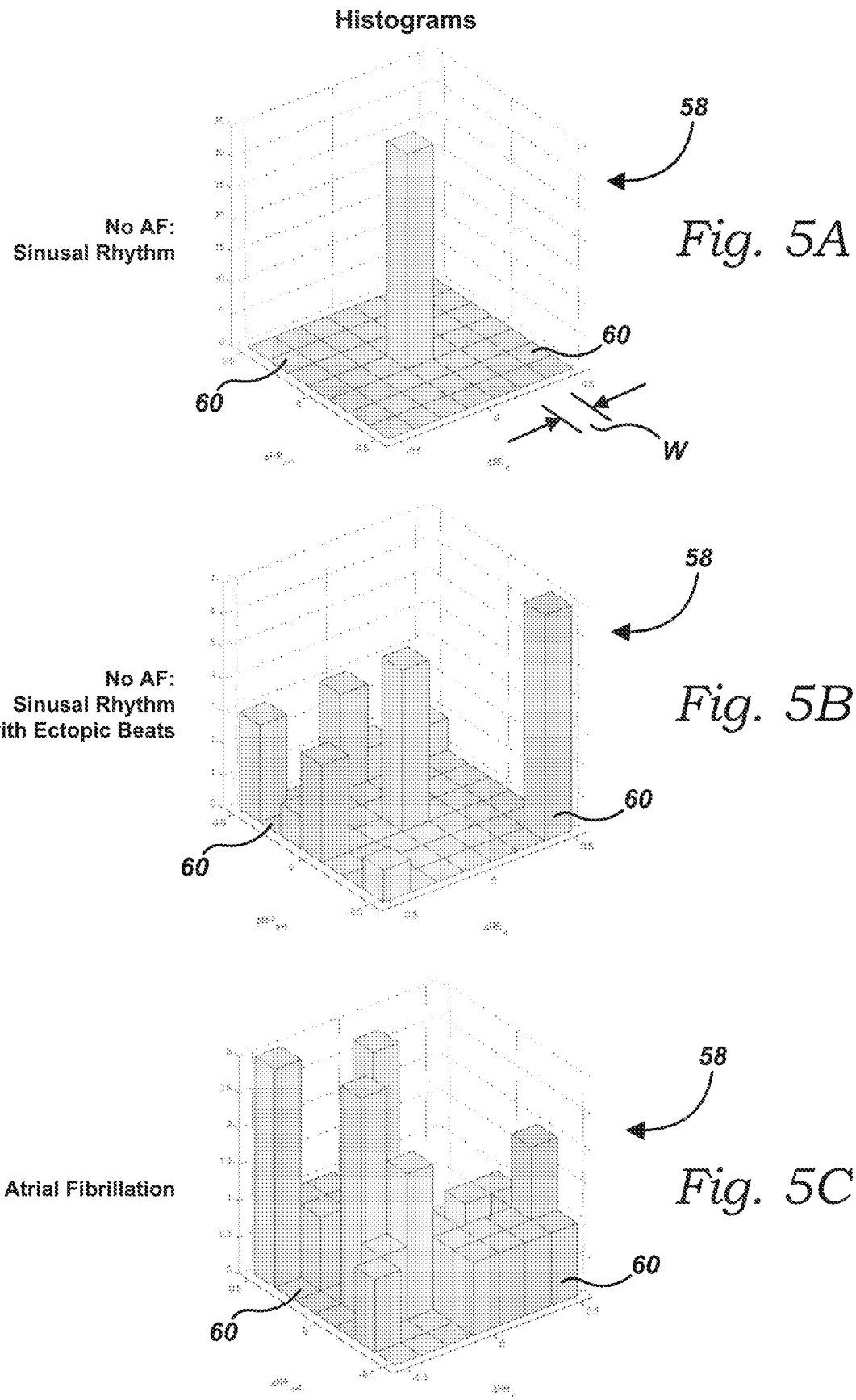

Matrix Views of Normalized Histograms

No AF:
Sinusal Rhythm

No AF:
Sinusal Rhythm
with Ectopic Beats

Atrial Fibrillation

ATRIAL FIBRILLATION DETECTION SYSTEM AND METHODS OF USE

RELATED APPLICATIONS

This application claims priority and is entitled to the filing date of ES application number P201531775—filed on Dec. 7, 2015. The contents of the aforementioned application is incorporated by reference herein.

BACKGROUND

The subject of this patent application relates generally to atrial fibrillation, and more particularly to an atrial fibrillation detection system and associated methods of use configured for analyzing and identifying atrial fibrillation signs.

Applicant(s) hereby incorporate herein by reference any and all patents and published patent applications cited or referred to in this application.

By way of background, atrial fibrillation ("AF") is an abnormal heart rhythm characterized by rapid and irregular beating, often starting as brief periods of abnormal beating and becoming longer and possibly constant over time. AF is associated with an increased risk of heart failure, dementia, and stroke. It is one of the most, if not the most, commonly sustained forms of arrhythmia, increasing in prevalence with the age of patients; from 0.5% at 40-50 years of age, to 5-15% at 80 years of age. Men are more often affected than women. The lifetime risk of developing AF is roughly 25% in those who have reached the age of 40.

AF usually progresses from short, rare episodes, to longer and more frequent attacks. Clinically, different types of AF are distinguished, based on the presentation and duration of the arrhythmia. Paroxysmal AF consists of self-terminating episodes, usually shorter than 48 hours. Persistent AF is present when an AF episode either lasts longer than 7 days or requires termination by cardioversion (either pharmacological or electrical). Long-standing persistent AF is considered so when it has lasted for more than 1 year. Permanent AF is said to exist when the presence of the arrhythmia is accepted both by the patient and the physician. In general terms, a patient is usually diagnosed from paroxysmal AF and as time goes on it will evolve to sustained forms of AF. The distribution of paroxysmal AF recurrences is not random, but clustered, and AF burden (the time ratio with and without AF) can vary markedly over months or even years in individual patients. Asymptomatic AF (silent AF) is common even in symptomatic patients, irrespective of whether the initial presentation was persistent or paroxysmal.

Rapid and irregular heart rates may be perceived as palpitations or exercise intolerance and occasionally may produce anginal chest pain (if the high heart rate causes ischemia). Other possible symptoms include congestive symptoms such as shortness of breath or swelling. The arrhythmia is sometimes only identified with the onset of a stroke or a transient ischemic attack ("TIA"). Additionally, AF episodes can self-terminate and the triggering situations of a new episode are not easily predictable. As such, it is not uncommon for a patient to first become aware of AF from a routine physical examination or ECG, as it often does not cause symptoms. It has been estimated that 7-day continuous ECG monitoring may document the arrhythmia in approximately 70% of AF patients. To process these long-term ECG signals, either real-time or offline, AF detection algorithms are needed. Thus, there is a need for systems and methods capable of detecting AF signs (i.e., able to distinguish between AF and non-AF rhythms) as early and accurately as possible, so that such patients may be promptly diagnosed and treated in order to effectively control the disease.

Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing an atrial fibrillation detection system and associated methods of use are disclosed for analyzing and identifying atrial fibrillation signs of a user. In at least one embodiment, the system includes an at least one computing device configured for receiving and processing an at least one biosignal associated with heart activity of the user as captured by an at least one beat detector, and subsequently transmitting said processed at least one biosignal, as a plurality of sequence segments, making up an at least one interbeat interval sequence of the biosignal, to an at least one classifier configured for determining a probability of the at least one interbeat interval sequence of the biosignal being an atrial fibrillation rhythm or a non-atrial fibrillation rhythm. Upon receiving the at least one biosignal from the at least one beat detector, the at least one computing device is further configured for representing each of an at least one beat of the biosignal with an univocal and repeatable point. An interbeat interval between each of the at least one beat and an immediately preceding beat of the biosignal is calculated. An at least one interbeat interval sequence is generated consisting of consecutive interbeat intervals of the biosignal. The interbeat interval sequence is divided into a plurality of finite sequence segments of a pre-defined temporal length consisting of consecutive interbeat intervals of the interbeat interval sequence. For each sequence segment, said sequence segment is encoded by generating a scatter plot that represents the dispersion of data associated with the interbeat interval sequence. The scatter plot is encoded by generating a histogram that represents an amount of plot points plotted in each particular region of the scatter plot. The histogram is normalized by dividing a bin count of each bin by the total sum of plot points in the scatter plot. The normalized histogram is transmitted to an at least one classifier in selective communication with the at least one computing device, where a probability of said sequence segment being an atrial fibrillation rhythm or a non-atrial fibrillation rhythm is determined.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIGS. 5A-5C are illustrations of exemplary histograms of the sequence segments of FIGS. 4A-4C, respectively, plotted on a three-dimensional graph, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
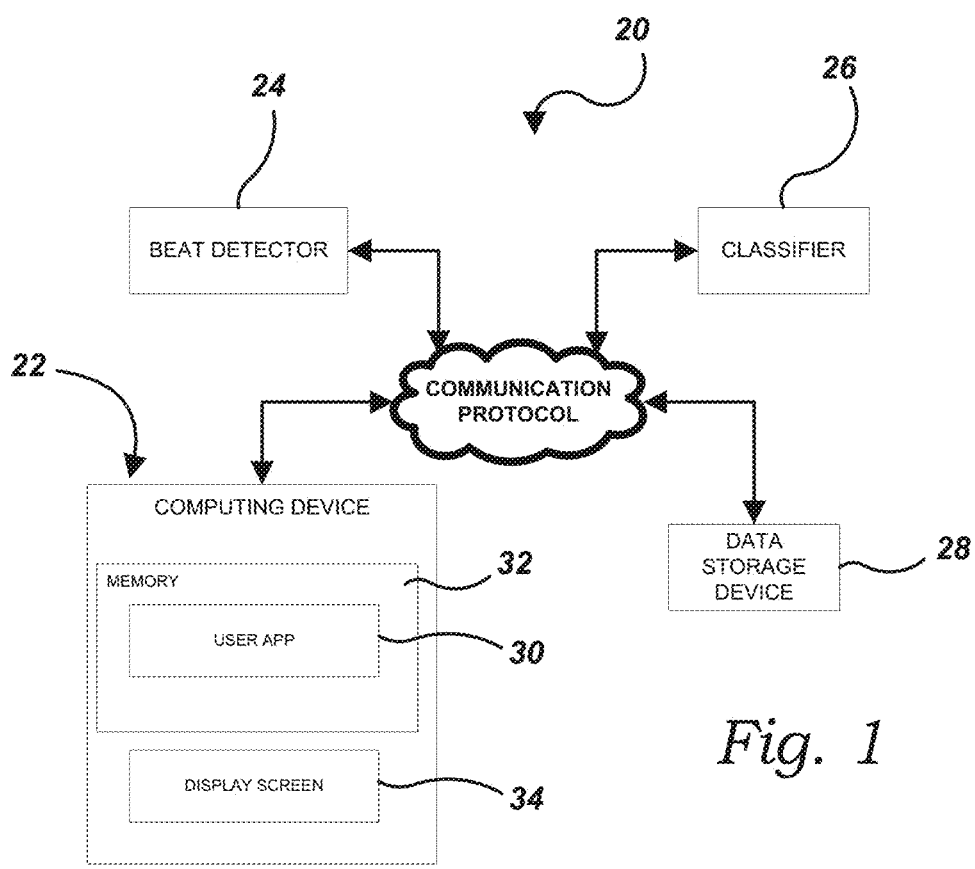
FIG. 1 is a simplified schematic view of an exemplary atrial fibrillation detection system, in accordance with at least one embodiment.

Turning now to FIG. 1, there is shown a simplified schematic view of an exemplary atrial fibrillation detection system 20. The system 20 provides, in at least one embodiment, an at least one computing device 22 configured for receiving and processing select data obtained by an at least one beat detector 24—such as an electrocardiogram ("ECG") device, for example (though any other type of device, sensor or combination thereof, now known or later developed, capable of substantially carrying out the functionality described herein may be substituted)—positioned and configured for obtaining biosignal data related to a user's heart activity (i.e., electrical activity of the user's heart). Accordingly, in at least one embodiment, the computing device 22 is in selective communication with the beat detector 24. In at least one embodiment, the computing device 22 and the beat detector 24 are one and the same—as such, it is intended that those terms as used herein are to be interchangeable with one another. Additionally, in at least one embodiment, an at least one classifier 26—such as an artificial neural network ("ANN"), for example (though any other type of device, system or combination thereof, now known or later developed, capable of substantially carrying out the functionality described herein may be substituted)—is in selective communication with the computing device 22 and configured for analyzing said data obtained by the at least one beat detector 24 and processed by the computing device 22, as discussed in detail below. In at least one embodiment, the computing device 22 and the classifier 26 are also one and the same—as such, it is intended that those terms as used herein are to be interchangeable with one another. Additionally, in at least one embodiment, an at least one data storage device 28 is in selective communication with the computing device 22 and configured for storing said data obtained by the beat detector 24, processed by the computing device 22, and analyzed by the classifier 26, along with certain other data as discussed further below. In at least one embodiment, the computing device 22 and data storage device 28 are also one and the same—as such, it is intended that those terms as used herein are to be interchangeable with one another.

At the outset, it should be noted that communication between each of the at least one computing device 22, at least one beat detector 24, at least one classifier 26, and at least one data storage device 28 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the term "computing device" is intended to include any type of computing or electronic device, now known or later developed, capable of substantially carrying out the functionality described herein—such as desktop computers, mobile phones, smartphones, laptop computers, tablet computers, personal data assistants, gaming devices, wearable devices, etc. As such, the system 20 should not be read as being limited to use with any one particular type of computing or electronic device, even though certain exemplary devices may be mentioned or shown herein for illustrative purposes.

With continued reference to FIG. 1, in at least one embodiment, the at least one beat detector 24 is positioned on a wearable device, such as garment or other accessory being worn by the user, such as described in at least U.S. Patent Application Publication No. 2013/0338472, the contents of which are hereby incorporated herein by reference. In still further embodiments, the at least one beat detector 24 may be appropriately positioned in contact with (or proximal to) the user using any other means now known or later developed. Again, in further embodiments, the at least one beat detector 24 may be any other type of device, sensor or combination thereof, now known or later developed, capable of substantially carrying out the functionality described herein. In at least one embodiment, the computing device 22 is also removably engagable with the user—either directly with the user's body or with a wearable device, such as a garment or other accessory being worn by the user. In at least one such embodiment, the beat detector 24 is positioned within the computing device 22. In an alternate embodiment, the computing device 22 is positioned elsewhere—either still local to the user or remotely, or even divided, with some of the functional units implemented in a computing device 22 local to the user and other units implemented in remote computer work stations.

In at least one embodiment, the computing device 22 contains the hardware and software necessary to carry out the exemplary methods for analyzing and identifying atrial fibrillation signs, as described herein. Furthermore, in at least one embodiment, the computing device 22 comprises a plurality of computing devices selectively working in concert with one another to carry out the exemplary methods analyzing and identifying atrial fibrillation signs, as described herein. In at least one embodiment, the computing device 22 provides a user application 30 residing locally in memory 32 on the computing device 22, the user application 30 being configured for selectively communicating with each of the at least one beat detector 24 and classifier 26, as discussed further below. It should be noted that the term "memory" is intended to include any type of electronic storage medium (or combination of storage mediums) now known or later developed, such as local hard drives, RAM, flash memory, secure digital ("SD") cards, external storage devices, network or cloud storage devices, integrated circuits, etc. In at least one embodiment, the computing device 22 provides an at least one display screen 34 configured for displaying the atrial fibrillation data, as discussed in detail below. In at least one such embodiment, the display screen 34 is a touchscreen.

In use, in at least one embodiment, the system 20 is capable of analyzing and identifying atrial fibrillation signs in users/patients—particularly, distinguishing between AF and non-AF rhythms—using information contained in a biosignal 36 associated with heart activity of the user (such as an ECG sequence, for example). In at least one embodiment, as illustrated in the flow diagram of FIG. 2, and as further illustrated in the exemplary schematic of FIG. 3A, a biosignal 36 associated with heart activity of the user is captured by the at least one beat detector 24 (202) and transmitted to the user application 30 of the computing device 22 (204). In at least one such embodiment, where the beat detector 24 is an ECG sensor or the like, the beat detector 24 senses and transmits raw ECG data, as the biosignal 36, to the computing device 22. In at least one embodiment, the user application 30 represents each of an at least one beat 38 of the biosignal 36 with an univocal and repeatable point 40 (206). In at least one such embodiment, the user application 30 selects the point 40 having a maximum absolute derivative value among the biosignal 36. In at least one further embodiment, other repeatable points 40 could be selected by the user application 30, such as an R-peak value or a maximum negative/positive derivative value for example.

Figure 2:
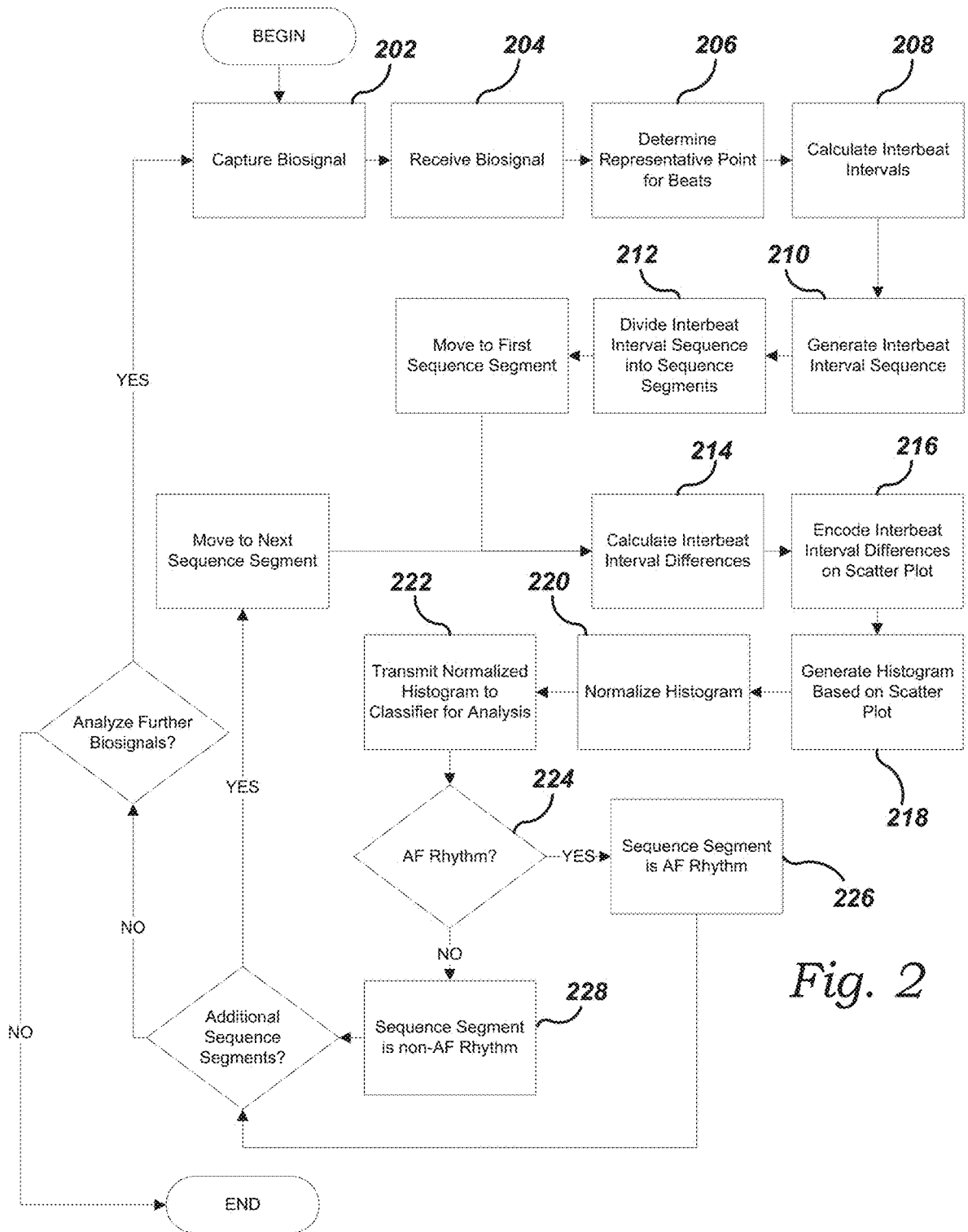
FIG. 2 is a flow diagram of an exemplary method for analyzing and identifying atrial fibrillation signs, in accordance with at least one embodiment.
Figure 3A:
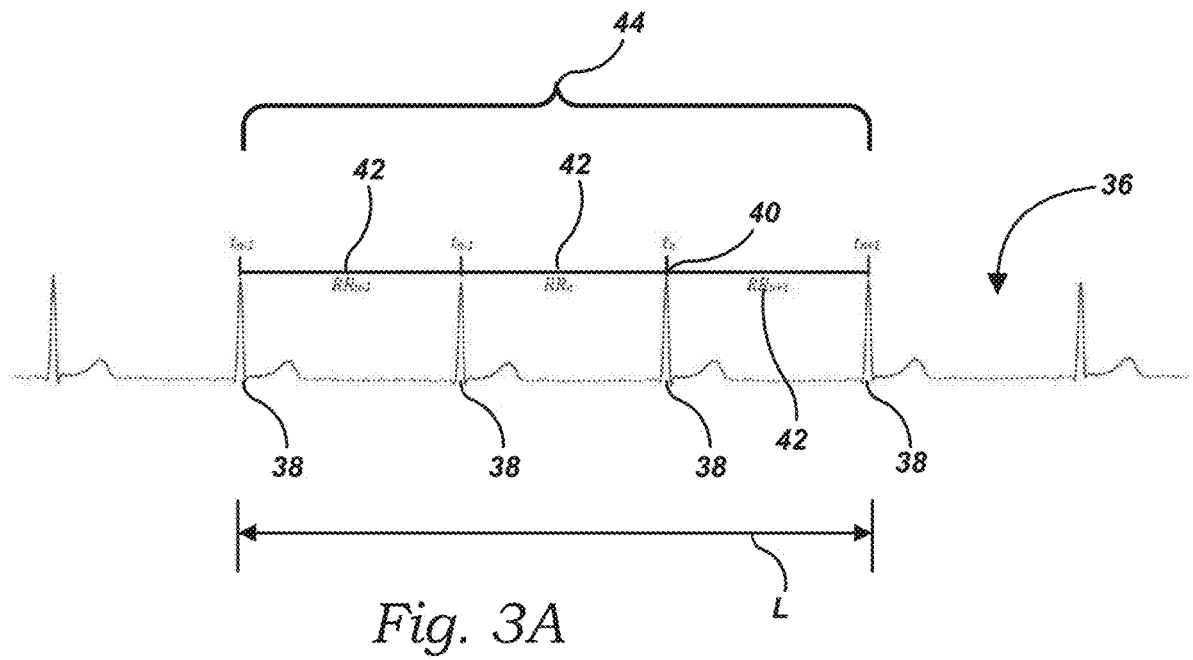
FIG. 3A is a schematic of an exemplary biosignal captured by an at least one beat detector of the exemplary atrial fibrillation detection system, in accordance with at least one embodiment.

With continued referenced to FIGS. 2 and 3A, in at least one embodiment, the user application 30 calculates an interbeat interval 42 ("$RR_n$") between each of the at least one beat 38 ("$t_n$") and an immediately preceding beat 38 ("$t_{n-1}$") of the biosignal 36 (208). In at least one such embodiment, the user application 30 uses the following formula: $RR_n = t_n - t_{n-1}$, where $t_n$ represents a timestamp of a current beat 38 n. In at least one embodiment, no processing is performed to smooth the biosignal 36 or remove any ectopic activity.

Figure 3B:
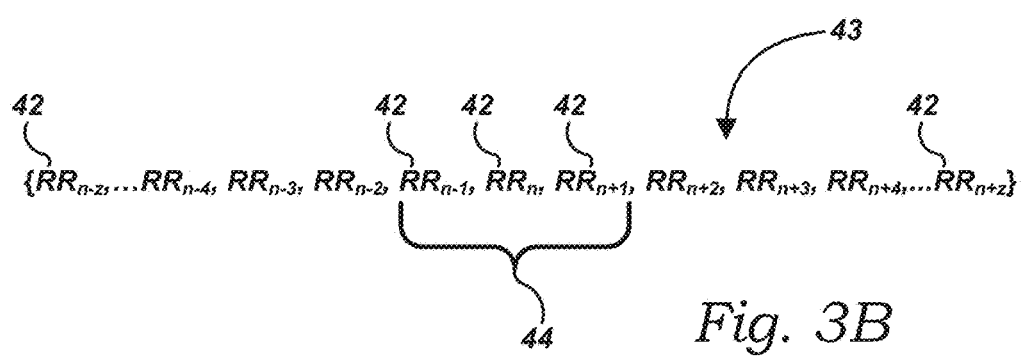
FIG. 3B is an illustration of an exemplary interbeat interval sequence, in accordance with at least one embodiment.

With continued reference to FIGS. 2 and 3A, and as further illustrated in FIG. 3B, in at least one embodiment, the user application 30 generates an at least one interbeat interval sequence 43 consisting of consecutive interbeat intervals 42 of the biosignal 36 (210). In at least one embodiment, the user application 30 divides the interbeat interval sequence 43 into a plurality of finite sequence segments 44 of a pre-defined temporal length L, consisting of consecutive interbeat intervals 42 of the interbeat interval sequence 43 and, in turn, the biosignal 36 (212). For example, in the exemplary embodiment, each sequence segment 44 has a length L of thirty (30) seconds. However, in further embodiments, any other length L deemed appropriate under the circumstances may be substituted without departing from the spirit or scope of the present invention. The user application 30 then encodes each sequence segment 44 by generating a two-dimensional scatter plot 46 that represents the dispersion of data associated with the interbeat interval sequence 43.

Figure 4A:
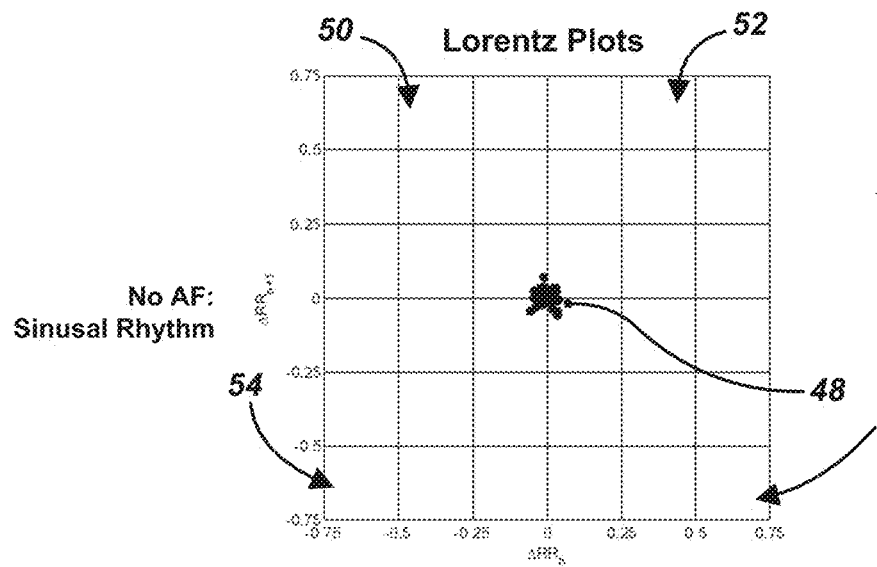
FIGS. 4A-4C are illustrations of exemplary Lorentz plots of sequence segments of exemplary interbeat interval sequences, plotted on a two-dimensional graph, in accordance with at least one embodiment.
Figure 4B:
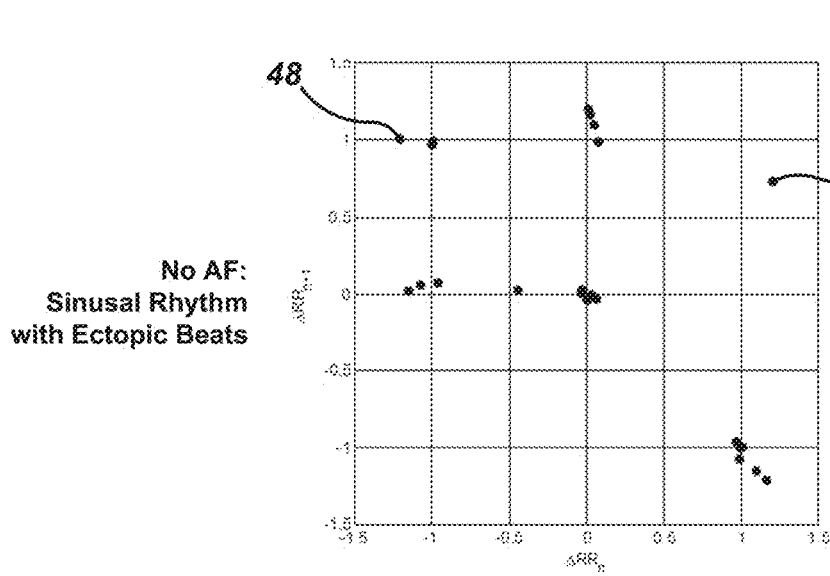
Figure 4C:
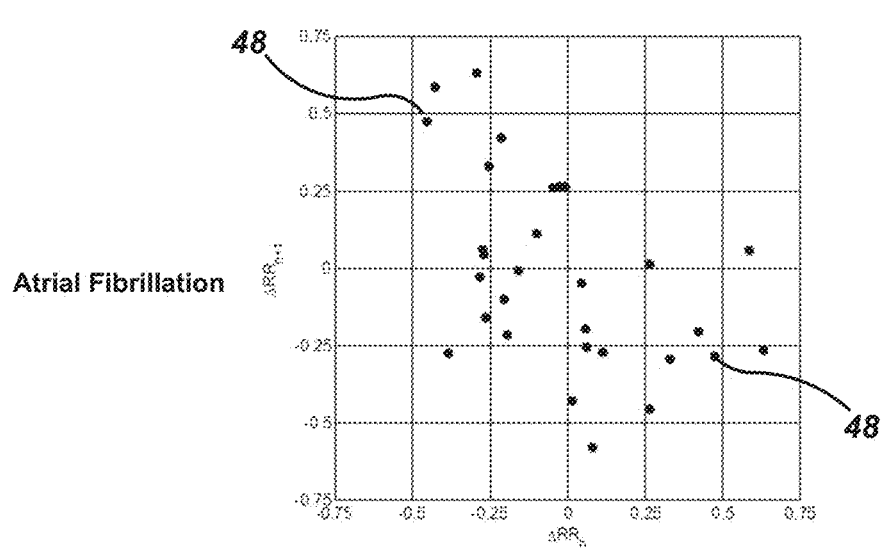

In a bit more detail and with continued reference to FIG. 2, in at least one embodiment, the user application 30 calculates an interbeat interval difference ("$\Delta RR_n$") between each of the at least one interbeat interval 42 ("$RR_{n+1}$") and an immediately preceding interbeat interval 42 ("$RR_n$") of the sequence segment 44 (214). In at least one such embodiment, the user application 30 uses the following formula: $\Delta RR_n = RR_{n+1} - RR_n$. In at least one embodiment, the user application 30 then encodes an uncorrelated nature of three consecutive interbeat interval differences as a plot point 48 on the scatter plot 46 (216), being a point defined as by the pair ($\Delta RR_n$, $\Delta RR_{n+1}$). In at least one such embodiment, as illustrated in FIGS. 4A-4C, the scatter plot 46 is a Lorentz plot. For example, if three consecutive interbeat interval differences are very similar, the corresponding plot point 48 will be near (0,0) on the scatter plot 46; for a short-medium-long sequence of three consecutive interbeat interval differences, the plot point 48 will be in a first quadrant 50 of the scatter plot 46; for a long-short-long sequence of three consecutive interbeat interval differences, the plot point 48 will be in a second quadrant 52 of the scatter plot 46; for a long-medium-short sequence of three consecutive interbeat interval differences, the plot point 48 will be in a third quadrant 54 of the scatter plot 46; and for a short-long-short sequence of three consecutive interbeat interval differences, the plot point 48 will be in a fourth quadrant 56 of the scatter plot 46. For illustrative purposes, FIG. 4A depicts an exemplary scatter plot 46 representing a sequence segment 44 having a length L of approximately thirty (30) seconds and containing a non-AF sinusal rhythm, FIG. 4B depicts a further exemplary scatter plot 46 representing a sequence segment 44 having a length L of approximately thirty (30) seconds and containing a non-AF sinusal rhythm with ectopic beats, and FIG. 4C depicts a still further exemplary scatter plot representing a sequence segment 44 having a length L of approximately thirty (30) seconds and containing an atrial fibrillation rhythm. It should be noted that in further embodiments, any other method of generating a dispersion or scatter plot 46 of the sequence segment 44, now known or later developed, may be substituted so long as such methods are capable of substantially carrying out the functionality described herein.

With continued reference to FIG. 2, in at least one embodiment, the user application 30 next encodes each scatter plot 46 by generating a histogram 58 (either two-dimensional or three-dimensional) that represents an amount of plot points 48 plotted in each particular region of the scatter plot 46 (218). In at least one embodiment, the histogram 58 contains a pre-defined number of bins 60, with the bins 60 each having a pre-defined bin width W. In at least one such embodiment, the histogram 58 contains forty-nine (49) bins 60, with each bin 60 having a bin width W of 150 milliseconds ("ms"). Additionally, in at least one such embodiment, the bins 60 are arranged in a matrix—such as a 7×7 matrix where the histogram 58 contains forty-nine (49) bins 60—as illustrated in FIGS. 5A-5C, which respectively continue the illustratives of FIGS. 4A-4C. In an alternate embodiment, the bins 60 are arranged in an array—such as an array of forty-nine (49) integers where the histogram 58 contains forty-nine (49) bins 60. In further embodiments, any other number of bins 60 and/or bin widths W deemed appropriate under the circumstances may be substituted without departing from the spirit or scope of the present invention.

Figure 6A:
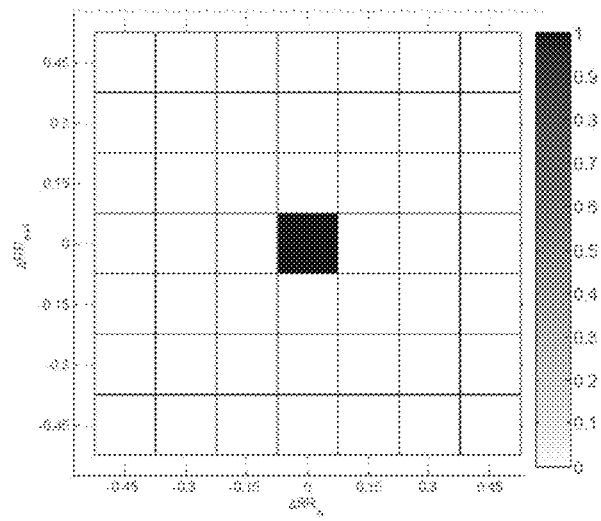
FIGS. 6A-6C are illustrations of exemplary matrix views of the normalized histograms of FIGS. 5A-5C, respectively, in accordance with at least one embodiment.
Figure 6B:
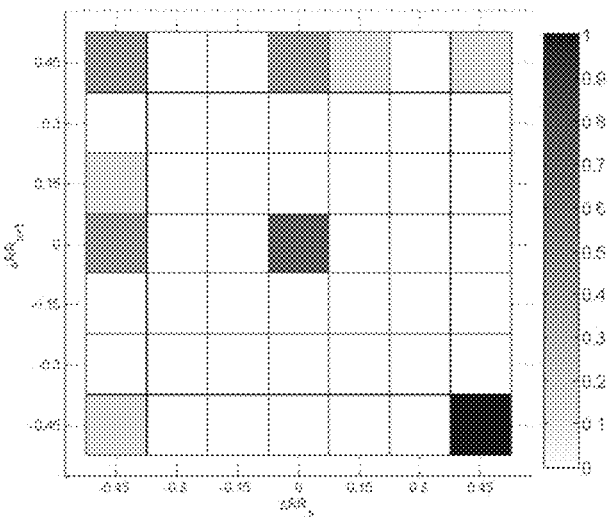
Figure 6C:
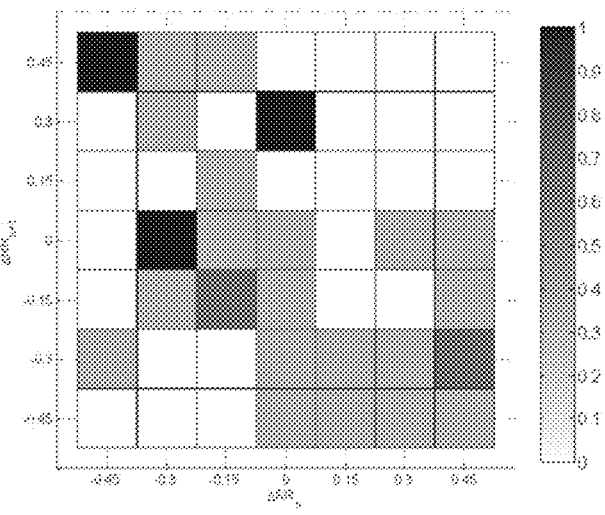

With continued reference to FIG. 2, in at least one embodiment, the user application 30 next normalizes the histogram 58 by dividing a bin count of each bin 60 by the total sum of plot points 48 in the scatter plot 46 (220)—as illustrated in FIGS. 6A-6C, which respectively continue the illustratives of FIGS. 4A-4C and 5A-5C. The normalized histogram 62 represents the sequence of interbeat interval differences of the consecutive interbeat intervals 42 that make up the sequence segment 44 of the interbeat interval sequence 43. In at least one embodiment, the user application 30 transmits the normalized histogram 62 to the at least one classifier 26 (222) which, in turn, analyzes the normalized histogram 62 to determine a probability of the sequence segment 44 of the interbeat interval sequence 43 (and, in turn, the associated portion of the biosignal 36) being an atrial fibrillation rhythm or non-AF rhythm (224). In at least one embodiment, if the classifier 26 determines that the probability of the sequence segment 44 being an atrial fibrillation rhythm is relatively greater than the probability of the sequence segment 44 being a non-AF rhythm, the user application 30 concludes that sequence segment 44 is an atrial fibrillation rhythm (226). Similarly, if the classifier 26 determines that the probability of the sequence segment 44 being a non-AF rhythm is relatively greater than the probability of the sequence segment 44 being an atrial fibrillation rhythm, the user application 30 concludes that the sequence segment 44 is a non-AF rhythm (228).

In at least one embodiment, as mentioned above, the classifier 26 is an artificial neural network ("ANN"). Additionally, the classifier 26 must be trained prior to performing the above-described method. In at least one such embodiment, the classifier 26 contains, or otherwise has access to, a database of a sufficient number of labeled instances of interbeat interval sequences 43 substantially representing an entire universe of possible rhythms—such as the MIT-BIH Atrial Fibrillation Database ("AFDB") and/or MIT-BIH Arrhythmia Database ("MITDB") for example—which allows the classifier 26 to automatically learn the inner rules that govern decisions. In at least one embodiment, the ANN uses rectified linear unit ("ReLU") hidden networks, softmax activation function for output neurons, and dropout and max-norm regularization in order to optimize the performance of the classifier 26. However, in further embodiments, any other type of ANN and/or ANN modifications, now known or later developed, may be substituted. In still further embodiments, rather than being an ANN, the classifier 26 may comprise any other type of device, system or combination thereof, now known or later developed, capable of substantially carrying out the functionality described herein.

Thus, in at least one embodiment, the classifier 26 is able to distinguish between AF and non-AF rhythms using the information contained in a thirty (30) second sequence segment 44 of the interbeat interval sequence 43 of a biosignal 36. As a result, in at least one such embodiment, every detected beat should be considered and no morphology assessment should be needed in order to eliminate ectopic beats that can potentially be confused with an AF rhythm. In this way, the system 20 is capable of being integrated in any beat analysis system (including ECG analysis systems) that performs beat detection, such as implantable or external cardiac monitors or offline analysis platforms such as Holter analysis software.

Aspects of the present specification may also be described as follows:

1. A method for analyzing and identifying atrial fibrillation signs of a user, the method comprising the steps of: transmitting to an at least one computing device an at least one biosignal associated with heart activity of the user as captured by an at least one beat detector; representing each of an at least one beat of the biosignal with an univocal and repeatable point; calculating an interbeat interval between each of the at least one beat and an immediately preceding beat of the biosignal; generating an at least one interbeat interval sequence consisting of consecutive interbeat intervals of the biosignal; dividing the interbeat interval sequence into a plurality of finite sequence segments of a pre-defined temporal length consisting of consecutive interbeat intervals of the interbeat interval sequence; and for each sequence segment: encoding said sequence segment by generating a scatter plot that represents the dispersion of data associated with the interbeat interval sequence; encoding the scatter plot by generating a histogram that represents an amount of plot points plotted in each particular region of the scatter plot; normalizing the histogram by dividing a bin count of each bin by the total sum of plot points in the scatter plot; transmitting the normalized histogram to an at least one classifier in selective communication with the at least one computing device; and determining, via the classifier, a probability of said sequence segment being an atrial fibrillation rhythm or a non-atrial fibrillation rhythm.

2. The method according to embodiment 1, wherein the step of representing each of the at least one beat of the biosignal with an univocal and repeatable point, further comprises the step of selecting a one of the points having a maximum absolute derivative value among the biosignal.

3. The method according to embodiments 1-2, wherein the step of dividing the interbeat interval sequence into a plurality of finite sequence segments of a pre-defined temporal length, further comprises the step of dividing the interbeat interval sequence into a plurality of finite sequence segments each having a length of thirty seconds.

4. The method according to embodiments 1-3, wherein the step of encoding said sequence segment by generating a scatter plot, further comprises the step of encoding said sequence segment by generating a two-dimensional scatter plot.

5. The method according to embodiments 1-4, wherein the step of encoding said sequence segment by generating a two-dimensional scatter plot, further comprises the steps of: calculating an interbeat interval difference between each of the at least one interbeat interval and an immediately preceding interbeat interval of said sequence segment; and encoding an uncorrelated nature of three consecutive interbeat interval differences as a plot point on the scatter plot.

6. The method according to embodiments 1-5, wherein the step of encoding said sequence segment by generating a two-dimensional scatter plot, further comprises the step of encoding said sequence segment by generating a two-dimensional Lorentz plot.

7. The method according to embodiments 1-6, wherein the step of encoding the scatter plot by generating a histogram, further comprises the step of generating a two-dimensional histogram that represents an amount of plot points plotted in each particular region of the scatter plot.

8. The method according to embodiments 1-7, wherein the step of encoding the scatter plot by generating a histogram, further comprises the step of generating a three-dimensional histogram that represents an amount of plot points plotted in each particular region of the scatter plot.

9. The method according to embodiments 1-8, wherein the step of generating a histogram further comprises the step of generating a histogram containing a pre-defined number of bins, with the bins each having a pre-defined bin width.

10. The method according to embodiments 1-9, further comprising the step of generating a histogram containing forty-nine bins, with each bin having a bin width of 150 milliseconds.

11. The method according to embodiments 1-10, further comprising the step of arranging the bins in a matrix.

12. The method according to embodiments 1-11, further comprising the step of arranging the bins in an array.

13. The method according to embodiments 1-12, wherein the step of transmitting the normalized histogram to an at least one classifier, further comprises the step of transmitting the normalized histogram to an at least one artificial neural network trained for analyzing the normalized histogram.

14. The method according to embodiments 1-13, wherein the step of determining, via the classifier, a probability of said sequence segment being an atrial fibrillation rhythm or a non-atrial fibrillation rhythm, further comprises the steps of: upon the classifier determining that the probability of said sequence segment being an atrial fibrillation rhythm is relatively greater than the probability of said sequence segment being a non-atrial fibrillation rhythm, concluding that said sequence segment is an atrial fibrillation rhythm; and upon the classifier determining that the probability of said sequence segment being a non-atrial fibrillation rhythm is relatively greater than the probability of said sequence segment being an atrial fibrillation rhythm, concluding that said sequence segment is a non-atrial fibrillation rhythm.

15. The method according to embodiments 1-14, further comprising the step of implementing an at least one data storage device in selective communication with the at least one computing device and configured for storing data captured by the at least one beat detector, processed by the at least one computing device, and analyzed by the at least one classifier.

16. The method according to embodiments 1-15, further comprising the step of positioning the at least one beat detector on a wearable device worn by the user.

17. The method according to embodiments 1-16, wherein the step of positioning the at least one beat detector further comprises the step of positioning an at least one electrocardiogram device on the wearable device worn by the user.

18. A method for analyzing and identifying atrial fibrillation signs of a user, the method comprising the steps of: transmitting to an at least one computing device an at least one biosignal associated with heart activity of the user as captured by an at least one beat detector; representing each of an at least one beat of the biosignal with an univocal and repeatable point; calculating an interbeat interval between each of the at least one beat and an immediately preceding beat of the biosignal; generating an at least one interbeat interval sequence consisting of consecutive interbeat intervals of the biosignal; dividing the interbeat interval sequence into a plurality of finite sequence segments of a pre-defined temporal length consisting of consecutive interbeat intervals of the interbeat interval sequence; and for each sequence segment: calculating an interbeat interval difference between each of the at least one interbeat interval and an immediately preceding interbeat interval of said sequence segment; encoding an uncorrelated nature of three consecutive interbeat interval differences as a plot point on a scatter plot; encoding the scatter plot by generating a histogram that represents an amount of plot points plotted in each particular region of the scatter plot, the histogram containing a pre-defined number of bins, with each bin having a pre-defined bin width; normalizing the histogram by dividing a bin count of each bin by the total sum of plot points in the scatter plot; transmitting the normalized histogram to an at least one classifier in selective communication with the at least one computing device; and determining, via the classifier, a probability of said sequence segment being an atrial fibrillation rhythm or a non-atrial fibrillation rhythm.

19. An atrial fibrillation detection system for analyzing and identifying atrial fibrillation signs of a user, the system comprising: an at least one computing device configured for receiving and processing an at least one biosignal associated with heart activity of the user as captured by an at least one beat detector, and subsequently transmitting said processed at least one biosignal to an at least one classifier configured for determining a probability of the biosignal being an atrial fibrillation rhythm or a non-atrial fibrillation rhythm; wherein, upon receiving the at least one biosignal from the at least one beat detector, the at least one computing device is further configured for: representing each of an at least one beat of the biosignal with an univocal and repeatable point; calculating an interbeat interval between each of the at least one beat and an immediately preceding beat of the biosignal; generating an at least one interbeat interval sequence consisting of consecutive interbeat intervals of the biosignal; dividing the interbeat interval sequence into a plurality of finite sequence segments of a pre-defined temporal length consisting of consecutive interbeat intervals of the interbeat interval sequence; and for each sequence segment: encoding said sequence segment by generating a scatter plot that represents the dispersion of data associated with the interbeat interval sequence; encoding the scatter plot by generating a histogram that represents an amount of plot points plotted in each particular region of the scatter plot; normalizing the histogram by dividing a bin count of each bin by the total sum of plot points in the scatter plot; transmitting the normalized histogram to an at least one classifier in selective communication with the at least one computing device; and determining, via the classifier, a probability of said sequence segment being an atrial fibrillation rhythm or a non-atrial fibrillation rhythm.

20. The atrial fibrillation detection system according to embodiment 19, wherein while representing each of the at least one beat of the biosignal with an univocal and repeatable point, the computing device is further configured for selecting a one of the points having a maximum absolute derivative value among the biosignal.

21. The atrial fibrillation detection system according to embodiments 19-20, wherein each of the sequence segments has a length of thirty seconds.

22. The atrial fibrillation detection system according to embodiments 19-21, wherein the scatter plot is a two-dimensional scatter plot.

23. The atrial fibrillation detection system according to embodiments 19-22, wherein the computing device is further configured for: calculating an interbeat interval difference between each of the at least one interbeat interval and an immediately preceding interbeat interval of said sequence segment; and encoding an uncorrelated nature of three consecutive interbeat interval differences as a plot point on the scatter plot.

24. The atrial fibrillation detection system according to embodiments 19-23, wherein the two-dimensional scatter plot is a Lorentz plot.

25. The atrial fibrillation detection system according to embodiments 19-24, wherein the histogram is a two-dimensional histogram.

26. The atrial fibrillation detection system according to embodiments 19-25, wherein the histogram is a three-dimensional histogram.

27. The atrial fibrillation detection system according to embodiments 19-26, wherein the histogram contains a pre-defined number of bins, with the bins each having a pre-defined bin width.

28. The atrial fibrillation detection system according to embodiments 19-27, wherein the histogram contains forty-nine bins, with each bin having a bin width of 150 milliseconds.

29. The atrial fibrillation detection system according to embodiments 19-28, wherein the bins of the histogram are arranged in a matrix.

30. The atrial fibrillation detection system according to embodiments 19-29, wherein the bins of the histogram are arranged in an array.

31. The atrial fibrillation detection system according to embodiments 19-30, wherein the at least one classifier is an artificial neural network trained for analyzing the normalized histogram.

32. The atrial fibrillation detection system according to embodiments 19-31, wherein the artificial neural network uses rectified linear unit hidden networks, softmax activation function for output neurons, and dropout and max-norm regularization in order to optimize the performance of the classifier.

33. The atrial fibrillation detection system according to embodiments 19-32, wherein while determining, via the classifier, a probability of said sequence segment being an atrial fibrillation rhythm or a non-atrial fibrillation rhythm, the computing device is further configured for: upon the classifier determining that the probability of said sequence segment being an atrial fibrillation rhythm is relatively greater than the probability of said sequence segment being a non-atrial fibrillation rhythm, concluding that said sequence segment is an atrial fibrillation rhythm; and upon the classifier determining that the probability of said sequence segment being a non-atrial fibrillation rhythm is relatively greater than the probability of said sequence segment being an atrial fibrillation rhythm, concluding that said sequence segment is a non-atrial fibrillation rhythm.

34. The atrial fibrillation detection system according to embodiments 19-33, further comprising an at least one data storage device in selective communication with the at least one computing device and configured for storing data captured by the at least one beat detector, processed by the at least one computing device, and analyzed by the at least one classifier.

35. The atrial fibrillation detection system according to embodiments 19-34, wherein the at least one beat detector is an electrocardiogram device.

36. The atrial fibrillation detection system according to embodiments 19-35, wherein the at least one beat detector is positionable on a wearable device worn by the user.

In closing, regarding the exemplary embodiments of the present invention as shown and described herein, it will be appreciated that an atrial fibrillation detection system and associated methods of use are disclosed and configured for analyzing and identifying atrial fibrillation signs. Because the principles of the invention may be practiced in a number of configurations beyond those shown and described, it is to be understood that the invention is not in any way limited by the exemplary embodiments, but is generally directed to an atrial fibrillation detection system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for analyzing and identifying atrial fibrillation signs of a user, the method comprising the steps of:
   receiving, via an at least one computing device, an at least one biosignal associated with heart activity of the user as captured by an at least one beat detector;
   the at least one computing device representing each of an at least one beat of the biosignal with an univocal and repeatable point;
   the at least one computing device calculating an interbeat interval between each of the at least one beat and an immediately preceding beat of the biosignal;
   the at least one computing device generating an at least one interbeat interval sequence consisting of consecutive interbeat intervals of the biosignal;
   the at least one computing device dividing the interbeat interval sequence into a plurality of finite sequence segments of a pre-defined temporal length consisting of consecutive interbeat intervals of the interbeat interval sequence; and for each sequence segment:
the at least one computing device encoding said sequence segment by generating a scatter plot that represents the dispersion of data associated with the interbeat interval sequence;
the at least one computing device encoding the scatter plot by generating a histogram that represents an amount of plot points plotted in each particular region of the scatter plot;
the at least one computing device normalizing the histogram by dividing a bin count of each bin by the total sum of plot points in the scatter plot;
the at least one computing device transmitting the normalized histogram to an at least one classifier in selective communication with the at least one computing device; and
the at least one computing device determining, via the classifier, a probability of said sequence segment being an atrial fibrillation rhythm or a non-atrial fibrillation rhythm.

2. The method of claim 1, wherein the step of representing each of the at least one beat of the biosignal with an univocal and repeatable point, further comprises the step of the at least one computing device selecting a one of the points having a maximum absolute derivative value among the biosignal.

3. The method of claim 1, wherein the step of dividing the interbeat interval sequence into a plurality of finite sequence segments of a pre-defined temporal length, further comprises the step of the at least one computing device dividing the interbeat interval sequence into a plurality of finite sequence segments each having a length of thirty seconds.

4. The method of claim 1, wherein the step of encoding said sequence segment by generating a scatter plot, further comprises the step of the at least one computing device encoding said sequence segment by generating a two-dimensional scatter plot.

5. The method of claim 4, wherein the step of encoding said sequence segment by generating a two-dimensional scatter plot, further comprises the steps of:
the at least one computing device calculating an interbeat interval difference between each of the at least one interbeat interval and an immediately preceding interbeat interval of said sequence segment; and
the at least one computing device encoding an uncorrelated nature of three consecutive interbeat interval differences as a plot point on the scatter plot.

6. The method of claim 5, wherein the step of encoding said sequence segment by generating a two-dimensional scatter plot, further comprises the step of the at least one computing device encoding said sequence segment by generating a two-dimensional Lorentz plot.

7. The method of claim 1, wherein the step of generating a histogram further comprises the step of the at least one computing device generating a histogram containing a pre-defined number of bins, with the bins each having a pre-defined bin width.

8. The method of claim 7, further comprising the step of the at least one computing device generating a histogram containing forty-nine bins, with each bin having a bin width of 150 milliseconds.

9. The method of claim 1, wherein the step of transmitting the normalized histogram to an at least one classifier, further comprises the step of the at least one computing device transmitting the normalized histogram to an at least one artificial neural network trained for analyzing the normalized histogram.

10. The method of claim 1, wherein the step of determining, via the classifier, a probability of said sequence segment being an atrial fibrillation rhythm or a non-atrial fibrillation rhythm, further comprises the steps of:
upon the classifier determining that the probability of said sequence segment being an atrial fibrillation rhythm is relatively greater than the probability of said sequence segment being a non-atrial fibrillation rhythm, the at least one computing device concluding that said sequence segment is an atrial fibrillation rhythm; and
upon the classifier determining that the probability of said sequence segment being a non-atrial fibrillation rhythm is relatively greater than the probability of said sequence segment being an atrial fibrillation rhythm, the at least one computing device concluding that said sequence segment is a non-atrial fibrillation rhythm.

11. A method for analyzing and identifying atrial fibrillation signs of a user, the method comprising the steps of:
receiving, via to an at least one computing device, an at least one biosignal associated with heart activity of the user as captured by an at least one beat detector;
the at least one computing device representing each of an at least one beat of the biosignal with an univocal and repeatable point;
the at least one computing device calculating an interbeat interval between each of the at least one beat and an immediately preceding beat of the biosignal;
the at least one computing device generating an at least one interbeat interval sequence consisting of consecutive interbeat intervals of the biosignal;
the at least one computing device dividing the interbeat interval sequence into a plurality of finite sequence segments of a pre-defined temporal length consisting of consecutive interbeat intervals of the interbeat interval sequence; and
for each sequence segment:
the at least one computing device calculating an interbeat interval difference between each of the at least one interbeat interval and an immediately preceding interbeat interval of said sequence segment;
the at least one computing device encoding an uncorrelated nature of three consecutive interbeat interval differences as a plot point on a scatter plot;
the at least one computing device encoding the scatter plot by generating a histogram that represents an amount of plot points plotted in each particular region of the scatter plot, the histogram containing a pre-defined number of bins, with each bin having a pre-defined bin width;
the at least one computing device normalizing the histogram by dividing a bin count of each bin by the total sum of plot points in the scatter plot;
the at least one computing device transmitting the normalized histogram to an at least one classifier in selective communication with the at least one computing device; and
the at least one computing device determining, via the classifier, a probability of said sequence segment being an atrial fibrillation rhythm or a non-atrial fibrillation rhythm.

12. An atrial fibrillation detection system for analyzing and identifying atrial fibrillation signs of a user, the system comprising:
an at least one computing device configured for receiving and processing an at least one biosignal associated with heart activity of the user as captured by an at least one beat detector, and subsequently transmitting said processed at least one biosignal to an at least one classifier configured for determining a probability of the biosignal being an atrial fibrillation rhythm or a non-atrial fibrillation rhythm;

wherein, upon receiving the at least one biosignal from the at least one beat detector, the at least one computing device is further configured for:
  representing each of an at least one beat of the biosignal with an univocal and repeatable point;
  calculating an interbeat interval between each of the at least one beat and an immediately preceding beat of the biosignal;
  generating an at least one interbeat interval sequence consisting of consecutive interbeat intervals of the biosignal;
  dividing the interbeat interval sequence into a plurality of finite sequence segments of a pre-defined temporal length consisting of consecutive interbeat intervals of the interbeat interval sequence; and
  for each sequence segment:
    encoding said sequence segment by generating a scatter plot that represents the dispersion of data associated with the interbeat interval sequence;
    encoding the scatter plot by generating a histogram that represents an amount of plot points plotted in each particular region of the scatter plot;
    normalizing the histogram by dividing a bin count of each bin by the total sum of plot points in the scatter plot;
    transmitting the normalized histogram to an at least one classifier in selective communication with the at least one computing device; and
    determining, via the classifier, a probability of said sequence segment being an atrial fibrillation rhythm or a non-atrial fibrillation rhythm.

13. The atrial fibrillation detection system of claim 12, wherein while representing each of the at least one beat of the biosignal with an univocal and repeatable point, the computing device is further configured for selecting a one of the points having a maximum absolute derivative value among the biosignal.

14. The atrial fibrillation detection system of claim 12, wherein each of the sequence segments has a length of thirty seconds.

15. The atrial fibrillation detection system of claim 12, wherein, for each sequence segment, the computing device is further configured for:
  calculating an interbeat interval difference between each of the at least one interbeat interval and an immediately preceding interbeat interval of said sequence segment; and
  encoding an uncorrelated nature of three consecutive interbeat interval differences as a plot point on the scatter plot.

16. The atrial fibrillation detection system of claim 12, wherein the histogram is a three-dimensional histogram containing a pre-defined number of bins, with the bins each having a pre-defined bin width.

17. The atrial fibrillation detection system of claim 16, wherein the histogram contains forty-nine bins, with each bin having a bin width of 150 milliseconds.

18. The atrial fibrillation detection system of claim 12, wherein the at least one classifier is an artificial neural network trained for analyzing the normalized histogram.

19. The atrial fibrillation detection system of claim 18, wherein the artificial neural network uses rectified linear unit hidden networks, softmax activation function for output neurons, and dropout and max-norm regularization in order to optimize the performance of the classifier.

20. The atrial fibrillation detection system of claim 12, wherein the at least one beat detector is an electrocardiogram device.

* * * * *